April 18, 1972 G. VERBEEK Plant Pat. 3,112
ROSE PLANT
Filed Jan. 7, 1970
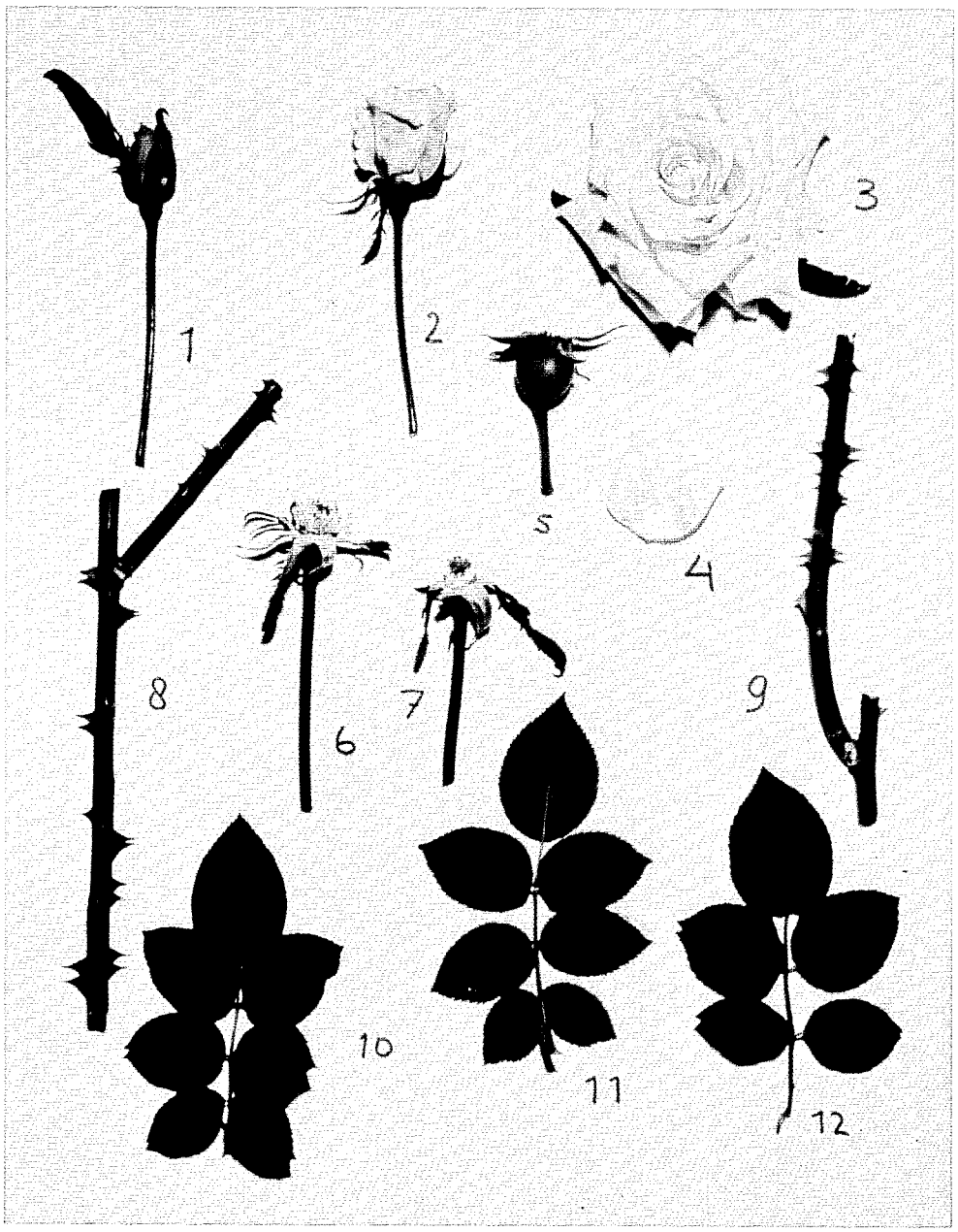

United States Patent Office

Plant Pat. 3,112
Patented Apr. 18, 1972

3,112
ROSE PLANT

Gijsbert Verbeek, Hornweg 109, Aalsmeer, Netherlands

Filed Jan. 7, 1970, Ser. No. 1,330
Int. Cl. A01h *5/00*
U.S. Cl. Plt.—18 1 Claim

ABSTRACT OF THE DISCLOSURE

A rose plant of the hybrid tea class, particularly for the greenhouse, originated by crossing the variety known as Miracle (Plant Patent No. 1863) with the variety known as Dr. A. J. Verhage (synonym Golden Wave) (Plant Patent No. 2,105).

SUMMARY OF INVENTION

The present invention relates to a new and distinct variety of rose plant of the hybrid tea class, which was originated by me by crossing the variety known as Miracle (Plant Patent No. 1,863) with the variety known as Dr. A. J. Verhage (synonym Golden Wave), (Plant Patent No. 2,105), the former being the seed parent and the latter being the pollen parent.

As the result of this breeding, I have produced a new and improved rose variety having the following unique combinations of characteristics which are outstanding therein and which distinguish it from its parents, as well as from all other varieties of which I am aware:

(1) A tall and upright, very vigorous habit of growth, with cutting stems of best length when grown under greenhouse conditions;

(2) Leaves with a leathery substance and good resistance to mildew;

(3) A more or less continuous production of flowers when grown under greenhouse conditions;

(4) Very long flower stems;

(5) A perfect shape of flower and a size ranging from medium to large;

(6) Good flower petalage;

(7) A high-centered flower form with long lasting qualities of flowers and long retention of the perfect form after opening;

(8) A very heavy perfume;

(9) A distinct and attractive flower color ranging between Dawn Pink and Venetian Pink.

In comparison with its seed parent Miracle, the new variety rarely produces more than a single flower to a stem, whereas the flowers of the seed parent are borne in groups.

As compared with its pollen parent Dr. A. J. Verhage (synonym Golden Wave) the new variety has a tall-growing habit, and the branches and stems of the new variety are much longer than those of the parent variety; the flowers of the new variety have much more petals as described hereafter.

Asexual reproduction of my new variety by budding and grafting, as performed at Aalsmeer, Netherlands, shows that the aforementioned characteristics and distinctions come true to form and are established and transmitted through succeeding propagations.

BRIEF DESCRIPTION OF THE DRAWINGS

The accompanying drawings show typical specimens of the vegetative growth and flowers of my new variety in different stages of development and as depicted in color as nearly true as it is reasonably possible to make the same in color illustration of this character, and wherein:

FIG. 1 shows the bud of the flower when just opening the sepals;

FIG. 2 shows the flowers when opening the first petals;

FIG. 3 shows the flower when completely opened;

FIG. 4 shows one of the petals;

FIG. 5 shows one of the hips still bearing the sepals at this stage;

FIG. 6 shows receptacle showing the stamens;

FIG. 7 shows receptacle showing the pistils after removing the stamens;

FIG. 8 shows one of the main branches;

FIG. 9 shows one of the branches that is ramified;

FIG. 10 shows one of the leaves with a composition of 7 leaflets showing the upper surface;

FIG. 11 shows one of the leaves with a composition of 7 leaflets showing the under surface; and FIG. 12 shows one of the leaves with a composition of 5 leaflets showing the upper surface.

DETAILED DESCRIPTION OF DISCLOSURE

The following is a detailed description of my new variety, with color terminology in accordance with the "Wilson Color Chart" I and II, published by the British Colour Council, except where general color terms of ordinary dictionary significance are obvious:

*Essential information*

Type: Hardy; bush; greenhouse; seedling; for cut flowers.
Class: Hybrid Tea.
Breeding: Seedling.
*Seed parent.*—Miracle.
*Pollen parent.*—Dr. A. J. Verhage (synonym Golden Wave).
Propagation: Holds its distinguishing characteristics through succeeding propagations by budding and grafting.

*Flower*

Locality where grown: Aalsmeer, Netherlands.
Flowers born: Singly to stem; on strong long stems.
Quantity of bloom: Abundant in greenhouse.
Continuity: Continuous during growing season.
Fragrance: Strong; Nature: Tea.
Bud:
*Peduncle.*—Average length; average caliper, erect, smooth with some gland-tipped cilia. Color—Lettuce Green HCC 861.
*Before calyx breaks.*—Size—Medium. Form—Medium length, ovoid, with a conspicuous neck; with foliaceous appendages on the surface of the bud; usually with foliaceous parts extending beyond the tip of the bud, equal to ½ of its length.
*As calyx breaks.*—Color—Coral Pink 0619/1.
*Sepals.*—Inner surface—with fine wooly tomentum; margins with foliaceous appendages, lined with gland-tipped cilia and glands.
*As first petals open.*—Size—average. Form—medium length, ovoid.
Color—outside—Carmine Rose 621/2. Inside—Carmine Rose 621/3. Opening—It does open up well.
Bloom:
*Size.*—When fully open—large, 4½ inches to 5 inches.
*Petalage.*—Very double, from 45 to 50 petals plus 4 to 6 petaloids; arranged regularly.
*Form.*—High-centered at first, becoming high-centered; petals remaining at first somewhat cupped with tips reflexed, outward; becoming later at maturity cupped with tips rolled outward.
Petals:
*Texture.*—Moderately leathery; with inside slightly satiny; outside slightly satiny.
*Shape.*—Outside—obovate with apex acute. Intermediate—obovate. Inside—obovate.

This description of a newly opened flower was made from a rose grown in a greenhouse in June 1969, at Aalsmeer, Netherlands.

*Color.—Outside petal*—outside surface: Dawn Pink HCC 523/3 at outer edges of petal shading into Neyron Rose HCC 623/3 toward base. Base of near Mimosa Yellow HCC 602/1; inside surface—Venetian Pink 420/1 with some shading of near Carmine Rose 621/2 towards base; base of Buttercup Yellow 5/1.

*Intermediate petal.*—outside surface: Geranium Lake 20/3 at outer edge of petal shading into Porcelain Rose 620/2. Base of near Begonia 619/1 shading into Amber Yellow 505/1; inside surface: Carmine Rose 621/3, base veined and shaded into Shrimp Red 616. *Inner petal*—outside surface: Begonia from 619/3 toward base into 619. Base Porcelain Rose 620; inside surface: Porcelain Rose 620/2 toward base 620/1. Base: Sulphur Yellow 1/2.

This description was made from a rose that was open for three days in a greenhouse in June 1969, at Aalsmeer, Netherlands.

*Color.—Outside petal*—outside surface: Azalea Pink 618/3 towards Scarlet 19/3; Base Primrose Yellow 601/3; inside surface: Venetian Pink 420/3 towards 420. Base: Sulphur Yellow 1/2. *Inside petal*—outside surface: Dawn Pink 523/3 towards 523/1; Base: Sulphur Yellow 1/2; inside surface: Coral Pink 0619/3 towards Coral Pink 0619/2, Base: Sulphur Yellow 1/2.

*General color effect.*—Newly opened flower—Empire Rose 0621/2. Three days open—French Rose 520.

*Behavior.*—Drop off cleanly.

*Flower longevity.*—Cut roses, grown in greenhouse and kept at living room temperature—8 days in June.

*Reproductive organs*

Stamens: Average number; arranged regularly about pistils and mixed a few with petaloids. Number: average: 90 to 100.

Filaments: Medium length.

Anthers: Medium size, all open at once approximately. Color upper side—buttercup yellow 5%1. Color under side—chrome yellow 605.

Pollen: Moderate quantity; color—buttercup yellow 5.

Pistils: Many; number—100 to 110.

Styles: Average caliper, separated. Color—Cardinal red 822/1.

Stigma: Color—Chinese yellow 606/2.

Ovaries: All enclosed in calyx.

Hips: Average length, globular with incospicuous neck. Color—green but turning yellow at maturity; smooth, walls thick.

Sepals: Falling soon, medium length, spear shaped, recurved. Color—inside: Scheels green 860/3; outside—Lettuce green 861/1.

Seeds: Average number, medium size.

*Plant*

Foliage:

*Leaves.*—Compound of usually 5–7 leaflets; normal; large size—leathery and glossy leaflets; shape—ovoid with apex acute. Base—round; margin—irregularly serrate.

*Color.—Mature* — upper surface: Ivy green 0001060/2; under surface — Lavender green 000761/1; *Young*—upper surface: Ivy green 0001060/1; under surface: Lavender green 000761/1.

*Rachis (the supporting stem of the compound leaf).*—Average size; upper side—grooved with some stipitate glands on edges; under side—moderately prickly.

*Stipules.*—Short, narrow, turning out at an angle of more than 45°.

*Disease.*—Good resistance to powdery mildew and blackspot.

Growth:

*Habit.*—Tall; bushy; upright; much branched.

*Growth.*—Very vigorous.

*Canes.*—Heavy.

Main stems:

*Color.*—Spinach green 0960/1.

*Large prickles.*—Several, medium length, hooked slightly downward; moderately base. Color—brown.

*Small prickles.*—None.

*Hairs.*—None.

Branches:

*Color.*—Spinach green 0960/3.

*Large prickles.*—Several, medium length, slightly downward; moderately base. Color—brown.

*Small prickles.*—Very few.

*Hairs.*—None.

New shoots:

*Color.*—Green with reddish overlay.

*Large prickles.*—Several, medium long, slightly downward; moderately base. Color—reddish purple.

*Small prickles.*—Very few.

*Hairs.*—None.

I claim:

1. A new and distinct variety of rose plant of the hybrid tea class, substantially as herein shown and described, characterized particularly as to novelty by the unique combination of a very vigorous and bushy habit of growth, with leaves of a leathery and very glossy substance with good mildew and blackspot resistance, suitable for greenhouse culture for commercial cut flowers, with very long stems, many flowers for year-round culture with best flower petalage, high centered flower form and long retention of this form, an attractive flower color ranging between Dawn Pink and Venetian Pink and heavy tea perfume and long-keeping qualities of the variety as cut flowers.

No references cited.

ROBERT E. BAGWILL, Primary Examiner